United States Patent [19]

Thompson et al.

[11] Patent Number: 5,633,405
[45] Date of Patent: May 27, 1997

[54] ASYMMETRIC SYNTHESIS OF (−)-6-CHLORO-4-CYCLOPROPYL-ETHYNYL-4-TRIFLUOROMETHYL-1,4-DIHYDRO-2H-3,1-BENZOXANZIN-2-ONE

[75] Inventors: Andrew S. Thompson, Mountainside; Edward G. Corley, Old Bridge; Edward J.J. Grabowski, Westfield; Nobuyoshi Yasuda, Mountainside, all of N.J.

[73] Assignee: Merck & Co., Inc., Rahway, N.J.

[21] Appl. No.: 450,330

[22] Filed: May 25, 1995

[51] Int. Cl.⁶ .................. C07C 211/00; C07C 51/16
[52] U.S. Cl. .................. 564/321; 564/387; 564/391; 558/410
[58] Field of Search .................. 564/391, 321, 564/387; 558/410

[56] References Cited

PUBLICATIONS

M.A. Huffman, et al., "Lithium Alkoxides of Cinchona Alkaloids as Chiral Controllers for Enantioselective Acetylidie Addition to Cyclic N–Acyl Ketimines", J. of Org. Chem, vol. 60(6) pp. 1590–1594 (1995).
Patent Abstract of JP4036252A.
K. Soai, et al., "Chiral N,N–Dialkylnorephedrines as Catalysts of the Highly Enantioselective Addition of Dialkylzines to Aliphatic and Aromatic Aldehydes. The Asymmetric Synthesis of Secondary Aliphatic and Aromatic Alcohols of High Optical Purity", J. Org. Chem., vol. 56(13) pp. 4264–4268, (1991).

Patent Abstracts of Japan, vol. 005(020), JP 55 145625, (1981).

O.M. Nefedov, et al., Chem. Abstracts, vol. 89(13), Abs. No. 108235, (1978).

Structure of RN136346–83–3 from J. Org. Chem. USSR, vol. 26 (10.2) vol. 26(10.2), pp. 1902–1904 (1990).

A.S. Thompson, et al., "Use of an Ephedrine Alkoxide to Mediate Enantioselective Addition of an Acetylide to a Prochiral Ketone: Asymmetric Synthesis of the Reverse Transcriptase Inhibitor" L–743,726., Tetrahedron Letts., vol. 36(49) pp. 8937–8940 (1995).

Mukaiyama, et al., "Enantioselective Addition of Acetylene to Aldehyde . . . ", Chemistry Letters, pp. 447–448, 1979.

Mukaiyama, et al., "Asymmetric Addition of Acetylide to Aliphatic Aldehydes . . . ", Chemistry Letters, pp. 255–256, 1980.

*Primary Examiner*—Mukund J. Shah
*Assistant Examiner*—Anthony Bottinc
*Attorney, Agent, or Firm*—Valerie J. Camara; Jack L. Tribble

[57] ABSTRACT

An improved synthesis of a highly potent HIV reverse transcription inhibitor is disclosed, involving an acetylide and a trifluoromethyl ketone which produces a chiral product in the presence of a chiral amino alcohol.

6 Claims, No Drawings

ASYMMETRIC SYNTHESIS OF (−)-6-CHLORO-4-CYCLOPROPYL-ETHYNYL-4-TRIFLUOROMETHYL-1,4-DIHYDRO-2H-3,1-BENZOXANZIN-2-ONE

BACKGROUND OF THE INVENTION

This case is related to Merck Case 18793IB which is a continuation-in-part of 18793IA, which is a continuation-in-part of Merck Case 18793, filed Aug. 7, 1992, U.S. Ser. No. 07/926,607 now abandoned, and 19345.

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is reverse transcription of the RNA genome by a virally encoded reverse transcriptase to generate DNA copies of HIV sequences, a required step in viral replication. It is known that some compounds are reverse transcriptase inhibitors and are effective agents in the treatment of AIDS and similar diseases, e.g., azidothymidine or AZT.

Nucleotide sequencing of HIV shows the presence of a pol gene in one open reading frame [Ratner, L. et al., *Nature*, 313, 277 (1985)]. Amino acid sequence homology provides evidence that the pol sequence encodes reverse transcriptase, an endonuclease and an HIV protease [Toh, H. et al., *EMBO J.*, 4, 1267 (1985); Power, M. D. et al., *Science*, 231, 1567 (1986); Pearl, L. H. et al., *Nature*, 329, 351 (1987)].

Applicants demonstrate a substantially improved synthesis of an inhibitor of HIV reverse transcriptase, of the structure

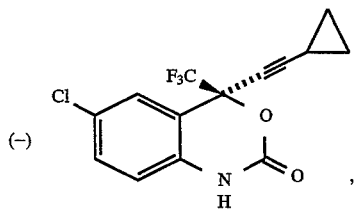

named (−) 6-Chloro-4-cyclopropylethynyl-4-trifluoromethyl-1,4-dihydro-2H-3,1-benzoxazin-2-one, hereinafter "Compound A." This compound is highly potent, even against HIV reverse transcriptase resistant to other AIDS antiviral compounds.

Applicants have devised an asymmetric synthesis of Compound A. Prior methods required a racemate penultimate product, with a lower overall yield. The present invention relates to a direct synthesis of the optically active Compound A, by chiral addition to a ketone intermediate to give a tertiary alcohol, with an enantiomeric excess of greater than 95%.

Further, it is unexpected that reaction of an acetylide with a trifluoromethyl ketone produces an optically active product. In the present invention, this is achieved with a chiral amino alcohol to mediate the addition reaction along an asymmetric pathway.

Applicants have also discovered that heating (followed by cooling) the mixture of lithiated chiral amino alcohol and cyclopropylacetylene, before the addition of the trifluoroketone, boosts the enantiomeric excess from about 85% in a typical run to more than about 95%. The unusually high levels of optical activity (>95% ee) make this method advantageous and practical.

BRIEF DESCRIPTION OF THE INVENTION

An improved synthesis of (−) 6-Chloro-4-cyclopropylethynyl-4-trifluoromethyl-1,4-dihydro-2H-3,1-benzoxazin-2-one is disclosed, and involves chiral addition to a ketone intermediate to give a tertiary alcohol. The compound is useful in the inhibition of HIV reverse tranriptase (and its resistant varieties), the prevention of infection by HIV, the treatment of infection by HIV and in the treatment of AIDS and/or ARC, either as compounds, pharmaceutically acceptable salts (when appropriate), pharmaceutical composition ingredients, whether or not in combination with other antivirals, anti-infectives, immunomodulators, antibiotics or vaccines. Methods of treating AIDS, methods of preventing infection by HIV, and methods of treating infection by HIV are also disclosed.

DETAILED DESCRIPTION OF THE INVENTION AND PREFERRED EMBODIMENTS

In this invention, there is disclosed a process for the asymmetric synthesis of the chiral compound of the structure

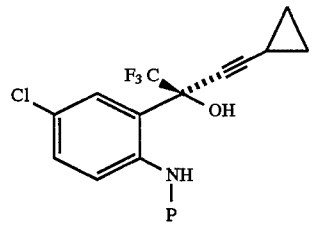

wherein P is an amino protecting group;
comprising the steps of:
  (a) providing a mixture of excess (1R,2S)-N-substituted norephedrine, of the structure

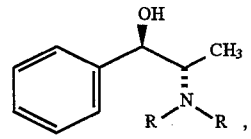

wherein R is $C_{1-4}$ alkyl, or —$NR_2$ forms pyrrolidinyl or piperidinyl;
with an excess of cyclopropylacetylene and an excess of a lithiating agent selected from n-butyllithium or sec-butyllithium or tert-butyllithium, at a temperature range of between about −78° C. and about 10° C., in aprotic solvent;
  (b) mixing with the mixture of Step (a) about one equivalent of reactant of the structure

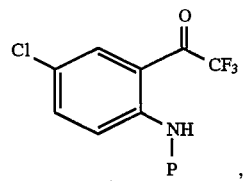

wherein P is an amino protecting group;
and maintaining the resulting reaction mixture at a temperature between about −78° C. and about −20° C.;

(c) quenching by adding a proton source;

(d) to give the desired compound.

One embodiment of this invention is a process of the asymmetric synthesis of the chiral compound N-(4-methoxybenzyl)-6-chloro-2-[(R)-cyclo-propyl-ethynyl-hydroxy-trifluoromethyl]-methylaniline, of the structure

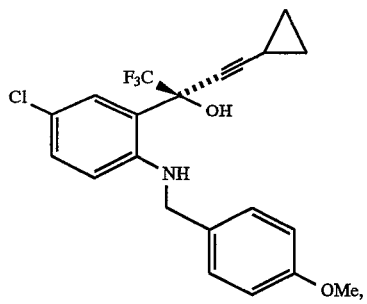

comprising the steps of:

(a) providing a mixture of excess (1R,2S)-N-substituted norephedrine, of the structure

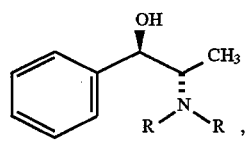

wherein R is $C_{1-4}$ alkyl, or —$NR_2$ forms pyrrolidinyl or piperidinyl;

with an excess of cyclopropylacetylene and an excess of a lithiating agent selected from n-butyllithium or sec-butyllithium or tert-butyllithium, at a temperature range between about −78° C. and about 10° C., in aprotic solvent;

(b) mixing with the mixture of Step (a) about one equivalent of reactant N-(4-methoxybenzyl)-6-chloro-2-(2-trifluoro-1-oxo-ethyl)-aniline, of the structure

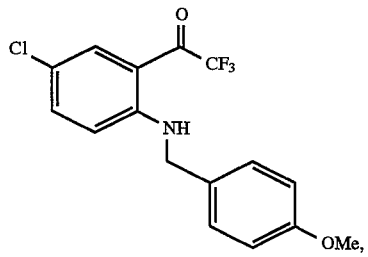

and maintaining the resulting reaction mixture at a temperature range of between about −78° C. and about −20° C.;

(c) quenching by adding a proton source;

(d) to give the desired compound.

Another embodiment of the same invention is a process for the asymmetric synthesis of the chiral compound of the structure

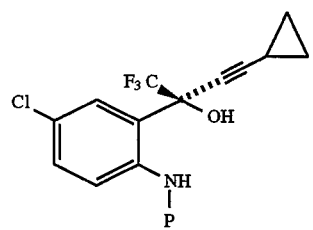

wherein P is an amino protecting group;
comprising the steps of:

(a) providing a mixture of excess (1R,2S)-N-pyrrolidinyl norephedrine, of the structure

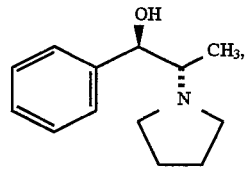

with an excess of cyclopropylacetylene and an excess of a lithiating agent selected from n-butyllithium or sec-butyllithium or tert-butyllithium, at a temperature of about −15° C., in aprotic solvent;

(b) mixing with the mixture of Step (a) about one equivalent of reactant of the structure

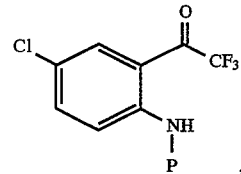

wherein P is an amino protecting group;
and maintaining the resulting reaction mixture at about −40° C.;

(c) quenching by adding a proton source;

(d) to give the desired compound.

Another embodiment of the same invention is a process for the asymmetric synthesis of the chiral compound N-(4-methoxybenzyl)-chloro-2-[(R)-cyclopropylethynyl-hydroxy-trifluoromethyl]-methylaniline, of the structure

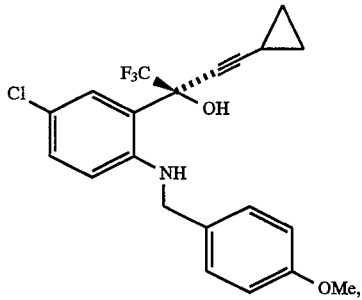

comprising the steps of:

(a) providing a mixture of excess (1R,2S)-N-pyrrolidinyl norephedrine, of the structure

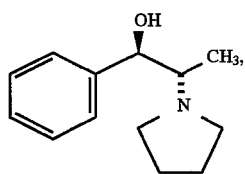

with an excess of cyclopropylacetylene and an excess of n-butyllithium, at a temperature of about −15° C., in aprotic solvent;

(b) mixing with the mixture of Step (a) about one equivalent of reactant N-(4-methoxybenzyl)-6-chloro-2-(2-trifluoro-1-oxo-ethyl)-aniline, of the structure

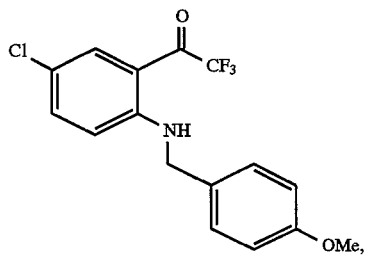

and maintaining the resulting reaction mixture at about −40° C.;

(c) quenching by adding a proton source;

(d) to give the desired compound, in ≧85% yield, ≧95% ee.

Any of the above processes may be modified to improve enantiomeric excess with an additional heating (followed by cooling) step between step (a) and step (b), that is, the mixture of step (a) is heated to between about −10° C. and about 10° C., for at least 5 minutes, then cooled to a temperature between about −78° C. and about −20° C., before the addition of the trifluoroketone. If the temperature of the mixture of step (a) already falls between about −10° C. and about 10° C., raising the temperature may not improve the enantiomeric excess.

One preferred modification for improving enantiomeric excess is with an additional heating (followed by cooling) step between step (a) and step (b), that is, the mixture of step (a) is heated to between about −10° C. and about 0° C., for between about 10 minutes and about 60 minutes, then cooled to a temperature of at least about −40° C., before the addition of the trifluoroketone.

This invention also covers a compound of the structure

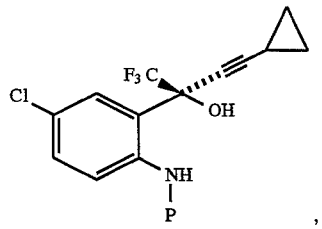

wherein P is an amino protecting group.

Another compound covered by this invention is N-(4-methoxybenzyl)-6-chloro-2-[(R)-cyclopropylethynyl-hydroxy-trifluoromethyl]-methyl-aniline, of the structure

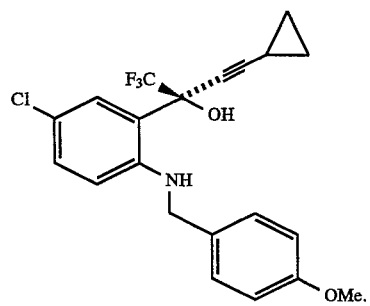

At first, excess (1R,2S)-N-substituted norephedrine is mixed in aprotic solvent with excess cyclopropylacetylene, and the acidic protons are removed by lithiation with an excess of n-BuLi or sec-butyllithium or tert-butyllithium. The resulting mixture is maintained at a temperature range between about −78° C. and about 10° C., preferably at about −15° C.

If the resulting mixture is heated to between about −10° C. and about 10° C., the product 6 is produced with substantially greater enantiomeric excess, typically about 95% instead of about 85% or less. Some aspects of this invention eliminate this heating step, others include it.

In the processes of this present invention, P is any suitable amino protecting group, and includes, but is not limited to, benzyl unsubstituted or substituted with $C_{1-4}$ alkyl; paramethoxy benzyl; para-nitrobenzyl; para-chlorobenzyl; 2,4-dichlorobenzyl; 2,4-dimethoxybenzyl; 4-methylsulfinyl benzyl; 9-anthrylmethyl; diphenylmethyl; or N-trialkylsilyl groups, according to T. W. Greene et al., *Protective groups in Organic Synthesis* 2nd Ed. John Wiley 1991, pp. 309–405. A preferable amino protecting group is para-methoxybenzyl. Once the reaction is initiated with the addition of about one equivalent of ketone 5, a trifluoroketone, the resulting reaction mixture is maintained between about −78° C. and about −20° C., preferably about −40° C. The reaction is carried out in aprotic solvent or ethereal solvent. Examples of aprotic solvents include THF, dioxane, $Et_2O$, benzene, DME, PheMe, n-octane, n-hexane, and cyclohexane, or mixtures thereof. One preferred solvent is THF. The incubation time of this reaction is at least 2–3 minutes after the addition of ketone.

At this point, the reaction mixture is quenched by addition of a proton source in aqueous medium, typically a mild acid. Any such proton source is suitable, e.g., one preferred proton source is 1M citric acid. Another is 1M acetic acid.

The chiral product 6 is purified by conventional techniques.

The compounds of the present invention may have asymmetric centers and may occur, except when specifically noted, as racemates, racemic mixtures or as individual diastereomers, or enantiomers, with all isomeric forms being included in the present invention. The term (+/−) is intended to encompass (+) optical isomers or (−) optical isomers or mixtures thereof.

When any variable (e.g., R) occurs more than one time in any constituent or in Formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms; if the number of carbon atoms is unspecified, "alkyl"

is intended to include 1 to 4 carbon atoms, both branched- and straight-chain saturated aliphatic hydrocarbon groups. "Halogen" or "halo" as used herein, means fluoro, chloro, bromo and iodo.

Compound A can be synthesized by the following method.

SCHEME I

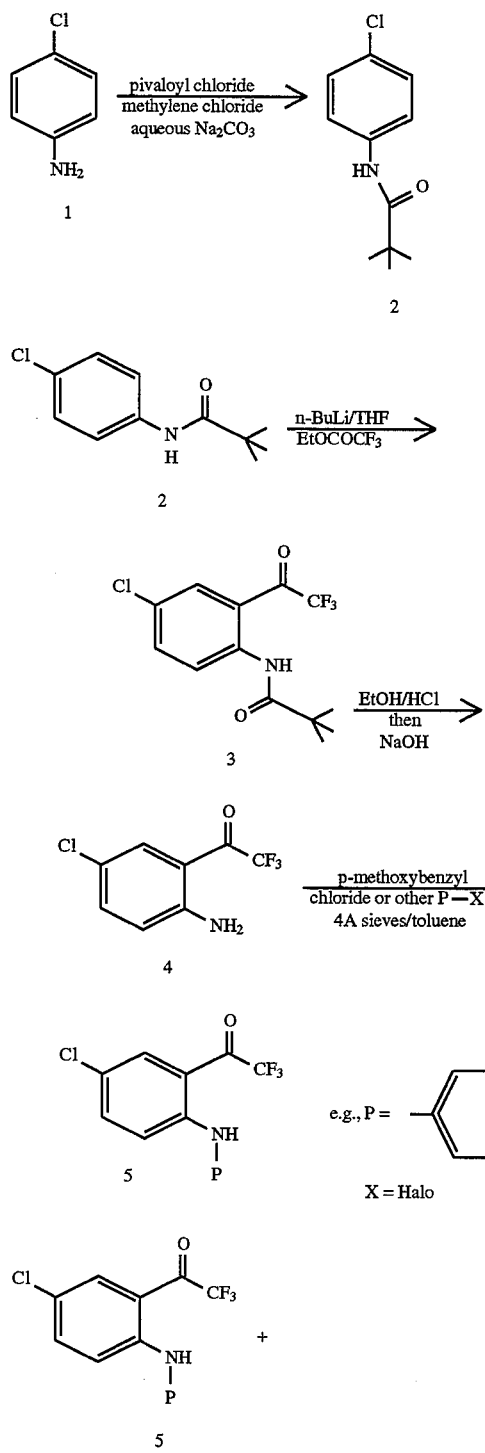

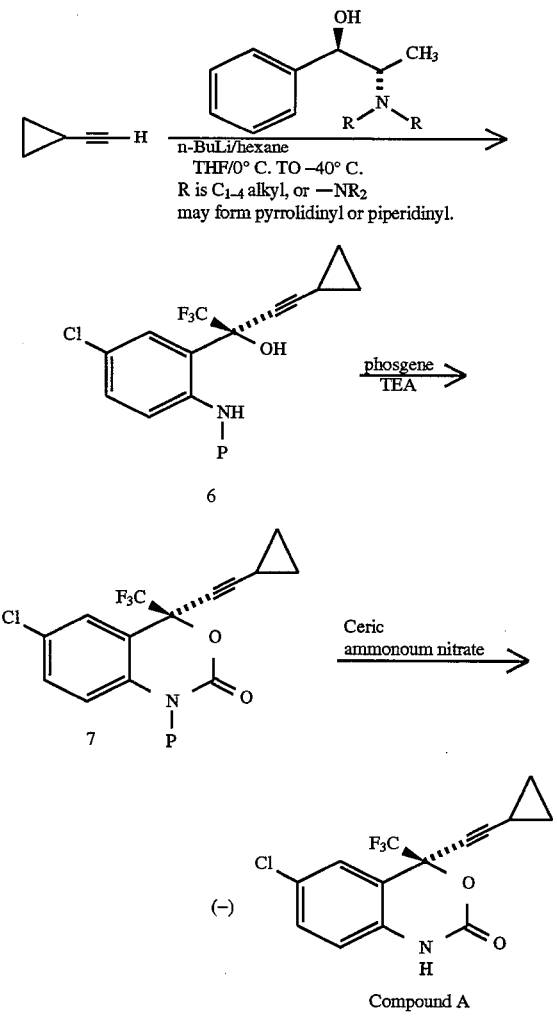

Cyclopropylacetylene, which is a reactant in the formation of 6, is prepared by the following alterative schemes;

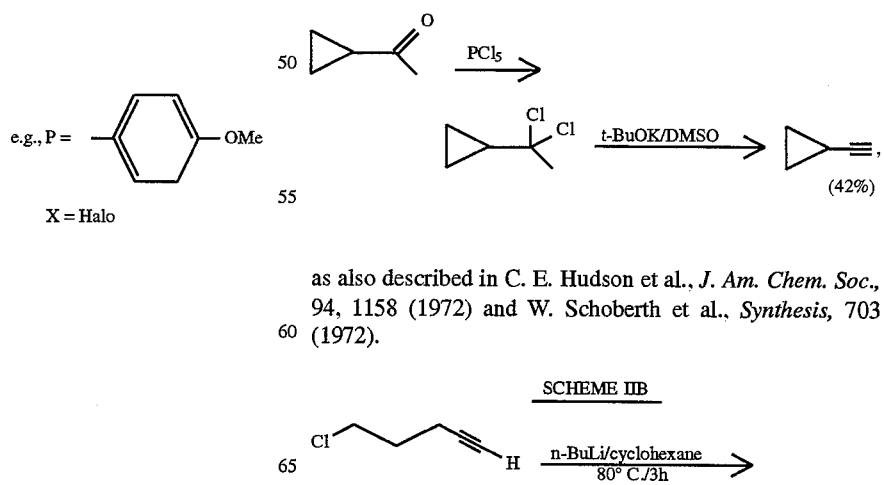

as also described in C. E. Hudson et al., *J. Am. Chem. Soc.,* 94, 1158 (1972) and W. Schoberth et al., *Synthesis,* 703 (1972).

-continued
SCHEME IIB

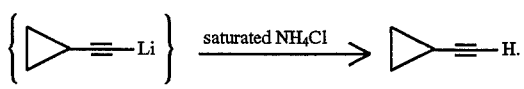

Scheme IIB is illustrated in Example 3, and is preferred.

Compound A is useful in the preparation and execution of screening assays for antiviral compounds. For example, Compound A is useful for isolating enzyme mutants, which are excellent screening tools for more powerful antiviral compounds. Furthermore, Compound A is useful in establishing or determining the binding site of other antivirals to HIV reverse transcriptase, e.g., by competitive inhibition. Thus Compound A is a commercial product to be sold for these purposes.

Compound A is useful in the inhibition of HIV reverse transcriptase, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, Compound A is useful in treating infection by HIV after suspected past exposure to HIV by e.g., blood transfusion, exchange of body fluids, bites, accidental needle stick, or exposure to patient blood during surgery.

The particular advantage of Compound A is its potent inhibition against HIV reverse transcriptase rendered resistant to other antivirals, such as L-697,661, which is 3-([(4, 7-dichloro-1,3-benzoxazol-2-yl)methyl]-amino)-5-ethyl-6-methyl-pyridin-2(1H)-one; or L-696,229, which is 3-[2-(1, 3-benzoxazol-2-yl)ethyl]-5-ethyl-6-methyl-pyridin-2(1H)-one; or AZT.

For these purposes, Compound A may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carders, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drag with a suitable non-irritating excipient, such as cocoa butter, synthetic glyceride esters or polyethylene glycols, which are solid at ordinary temperatures, but liquidify and/or dissolve in the rectal cavity to release the drug.

Compound A can be administered orally to humans in a dosage range of 1 to 100 mg/kg body weight in divided doses. One preferred dosage range is 0.1 to 10 mg/kg body weight orally in divided doses. Another preferred dosage range is 0.1 to 20 mg/kg body weight orally in divided doses. For combination therapy with nucleoside analogs, a preferred dosage range is 0.1 to 20 mg/kg body weight for the compounds of this invention administered orally in divided doses, and 50 mg to 5 g/kg body weight for nucleoside analogs administered orally in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drag combination, the severity of the particular condition, and the host undergoing therapy.

EXAMPLE 1

Preparation of 4-chlorophenyl-pivalamide

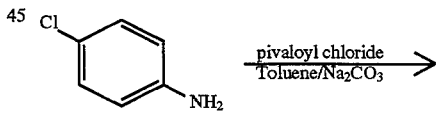

$C_6H_6ClN$
MW = 127.99

1

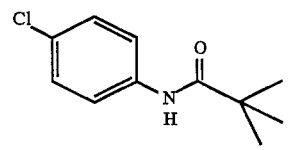

$C_{11}H_{14}ClNO$
MW = 211.66

2

| Materials | Amt | MMole | MW |
|---|---|---|---|
| 4-chloroaniline | 76 gm | 596 | 127.57 |
| Pivaloyl chloride (d = 0.979) | 74 ml | 600 | 120.58 |
| toluene | 600 ml | | |

| | |
|---|---|
| saturated Na₂CO₃ | 95 ml |
| D.I. water | 225 ml |

To a solution of 4-chloroaniline (76 gm) in toluene (600 ml) was added saturated Na₂CO₃ (95 ml). The batch was cooled to 10° C. and pivaloyl chloride (74 ml) was added dropwise over 45 minutes. The batch was stirred at 5°–10° C. for 60 minutes while the progress of the reaction was monitered by HPLC.

Addition of pivaloyl chloride to the aniline was exothermic.

HPLC conditions: C-8 column, CH₃CN, water, phosphoric acid; gradient elution from 40:60:0.1 to 80:20 0.1 over 20 minutes, flow=1.0 ml/min, UV detection at 245 nm, starting material $t_R$=7.2 min, pivalamide $t_R$=2.6 min.

The product was isolated by filtration and washed with D.I. water (3×75 ml) and air dried under suction for 10 minutes. The product was dried in a vacuum oven at 40° C. with an N₂ purge for 16 h to afford 108.5 gm of product as fine white needles (86%).

EXAMPLE 2

Preparation of 4-chloro-keto-aniline 4

C₁₁H₁₄ClNO
MW = 211.66
2

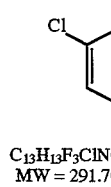
C₁₃H₁₃F₃ClNO
MW = 291.70
3

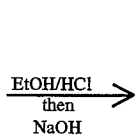

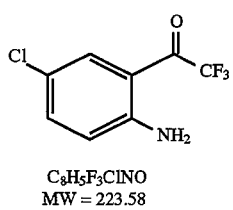
C₈H₅F₃ClNO
MW = 223.58
4

| Materials | Amt | MMole | MW |
|---|---|---|---|
| 4-chlorophenyl-pivalamide | 10 gm | 47.2 | 211.69 |
| n-BuLi/hexane (2.5M) | 38 ml | 95 | |
| ethyl trifluoroacetate (d = 1.194) | 6.7 ml | 56.6 | 142.08 |
| THF | 75 ml | | |
| Ethanol | 90 ml | | |
| 6N HCl | 50 ml | 240 | |
| hexane | 90 ml | | |
| 2N NaOH | 15 ml | | |
| D.I. water | 350 ml | | |

In a 500 ml 3 necked flask the pivalamide (10 gm) was dissolved in dry THF (75 ml) and the mixture was cooled to 0° C. To this solution was added n-BuLi/hexane (2.5M, 38 ml) dropwise while allowing the internal temperature to rise to +15° C. The batch was aged at 0° C. for 2 h.

Addition of the first equivalent of n-BuLi to the pivalamide was highly exothermic. The exotherm was controlled by the rate of addition.

To the resulting light yellow suspension was added neat ethyl trifluoroacetate (6.7 ml), while allowing the internal temperature to rise to +10° C. The progress of the reaction was monitored by HPLC.

HPLC conditions: C-8 column, CH₃CN, water, phosphoric acid; gradient elution from 40:60:0.1 to 80:20 0.1 over 20 minutes, flow=1.0 ml/min, UV detection at 245 nm, starting pivalamide $t_R$=12.6 min, keto-pivalamide $t_R$=11.6 min. There was typically 85A% product and 10–15A% unreacted pivalamide.

The reaction was quenched by adding 6N HCl (10 ml) and D.I. water (20 ml).

HPLC assay at this point showed 13.1 gm (90%) of product.

The solution was concentrated to ca. 50 ml in vacuo, and flushed with ethanol (50 ml) to remove hexane and THF. To the batch was added 6N HCl (40 ml) and the mixture was heated to reflux (80° C.) for 1 h.

HPLC assay shows 85–90A% of the keto-aniline, 10A% unreacted pivalamide. Thus the acylated material undergoes hydrolysis while unreacted pivalamide remains unchanged. The assay yield at this point was 7.78 gm (74%).

The batch was concentrated to ca. 50 ml in vacuo, at which time a precipitate formed (presumably the HCl salt of the product). The distillation was discontinued and the batch was cooled to 0° C. After a 1 h age, the batch was filtered and washed with hexane (3×30 ml).

The hexane washes remove unreacted pivalamide from the product. The solid is checked by HPLC to ensure it has been completely removed at this point. The filtrate and washes typically contain 1.2–1.5 gm of product (8–12%). The majority of product loss was in the aqueous filtrate.

The salt was dried in a vacuum oven at 40° C. for 16 h to afford 10.4 gm of a solid which was 71.4% pure by weight (70% yield). The salt was slurried in D.I. water (260 ml) and neutralized to a pH of ca. 6–7 with 2N NaOH (15 ml).

It was critical not to bring the pH above 9.0 due to product decomposition.

The resulting bright yellow solid was isolated by filtration and washed with D.I. water (2×25 ml). The product was dried in a vacuum oven at 40° C. for 16 h to afford 6 gm of keto aniline which was 96.6% pure by weight (54% yield).

The product is further purified by recrystallization from hexane.

EXAMPLE 3

Preparation of a N-4-methoxybenzyl-keto-aniline 5

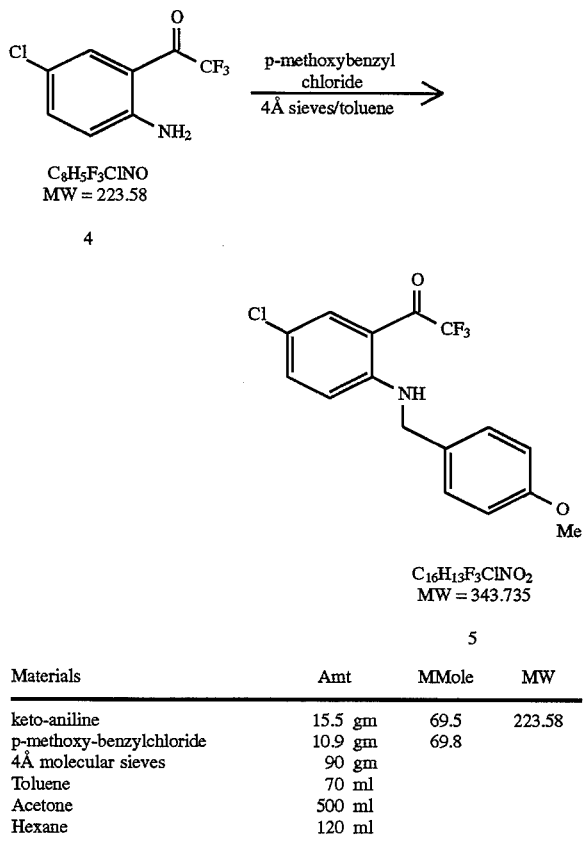

| Materials | Amt | MMole | MW |
|---|---|---|---|
| keto-aniline | 15.5 gm | 69.5 | 223.58 |
| p-methoxy-benzylchloride | 10.9 gm | 69.8 | |
| 4Å molecular sieves | 90 gm | | |
| Toluene | 70 ml | | |
| Acetone | 500 ml | | |
| Hexane | 120 ml | | |

In a 250 ml flask was charged the keto-aniline (15.5 gm), activated 4Å molecular sieves (50 gm) and toluene (75 ml). The mixture was stirred at 23° C. under $N_2$ for 24 h. Assay by HPLC showed ca. a 1:1 mixture of product and starting material.

HPLC conditions: C-8 column, $CH_3CN$, water, phosphoric acid; isocratic elution at 65:35:0.1 over 20 minutes, flow=1.0 ml/min, UV detection at 260 nm, toluene $t_R$=5.7 min, starting keto-aniline $t_R$=6.5 min, product $t_R$=15.0 min. There was typically 25A% of toluene.

The reaction was charged with fresh molecular sieves (40 gm) and stirred for an additional 3 days at 23° C. The reaction was judged complete when less than 2A% of starting material remained.

Alternatively, basic alumina or silica gel may be used in place of sieves to remove HCl from the system.

The mixture was filtered through celite and washed with acetone (7×75 ml) until most of the yellow color was washed from the celite. The filtrate was concentrated to afford 27 gm of a yellow-orange oil which solidified on standing. The solid was purified by dissolving it in hot hexanes (100 ml). The batch was cooled to rt, then to 0° C. in an ice-$H_2O$ bath. After a 1.5 h age, the batch was filtered and washed with cold hexanes (2×10 ml). The batch was air dried with suction for 10 minutes, then dried in a vacuum oven at 40° C. for 2 h. This afforded 20.5 gm (86%) of a bright yellow powder.

EXAMPLE 4

Preparation of cyclopropylacetylene

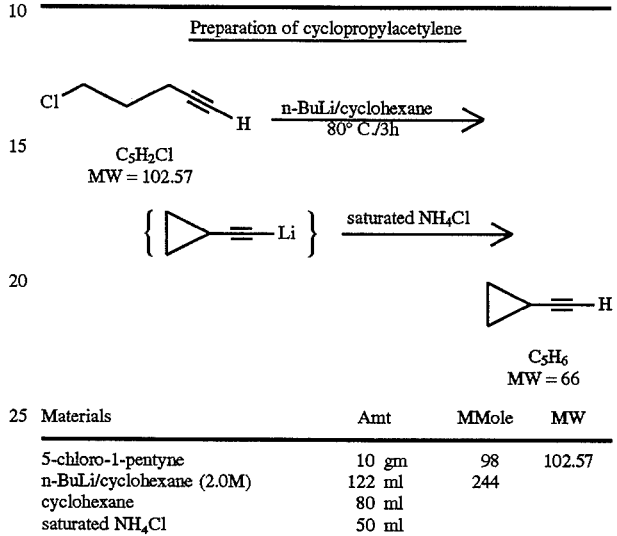

| Materials | Amt | MMole | MW |
|---|---|---|---|
| 5-chloro-1-pentyne | 10 gm | 98 | 102.57 |
| n-BuLi/cyclohexane (2.0M) | 122 ml | 244 | |
| cyclohexane | 80 ml | | |
| saturated $NH_4Cl$ | 50 ml | | |

To a solution of 5-chloro-1-pentyne in cyclohexane (80 ml) at 0° C. under $N_2$ was added n-butyllithium in cyclohexane (2.0M, 122 ml). The mixture was heated to 75° C. for 5 h.

Addition of n-butyllithium to the alkyne was exothermic, the temperature was maintained below +5° C. during these additions using an ice-$H_2O$ bath.

The progress of the cyclization step was monitored by HPLC. The reaction was considered complete when the assay yield was >90%.

HPLC conditions: Phenyl column, $CH_3CN$, water, phosphoric acid; 50:50:0.1 isocratic elution for 20 minutes, flow=1.0 ml/min, UV detection at 195 nm, starting material $t_R$=7.5 min, cylopropylacetylene $t_R$=6.0 min. The product has a response factor which was 20 times greater than the starting material.

Once the cyclization step was complete, the reaction was cooled to 0° C. and quenched with saturated $NH_4Cl$.

Assay of the organic phase by HPLC showed 5.5 gm of cyclopropylacetylene (85% yield).

The product was purified by fractional distillation through a 6"×0.5" column packed with 4 mm glass beads. The fraction with a boiling point between 45°–75° C. was collected.

This afforded 4.2 gm (65%) of cyclopropylacetylene as a colorless oil.

EXAMPLE 5

Preparation of the Amino Alcohol

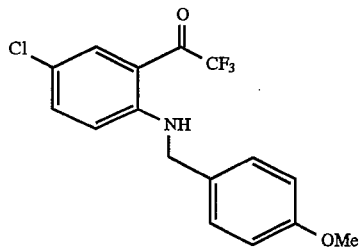

C₁₆H₁₃F₃ClNO₂
MW = 343

5

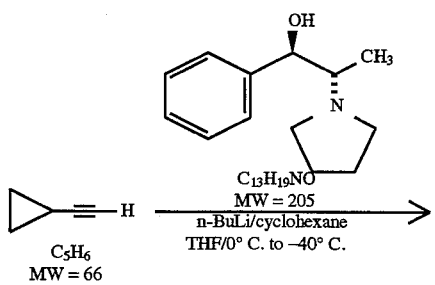

The pyrrolidinyl ephedrine (13.1 gm) was dissolved in THF (55 mL) and the mixture was cooled to −15° C. To the mixture at −15° C. under N₂ was added neat cyclopropylacetylene (5.3 mL) and n-butyllithium (50 mL) dropwise. The mixture was aged at −5 to 0° C. for 30 minutes, then cooled to −55° C.

The addition of n-butyllithium caused an exotherm which was maintained between −5° to 0° C. by the rate of addition.

The ketone (10 gm) was dissolved in THF (25 mL) under N₂ and added to the anionic mixture over 15 minutes allowing the internal temperature to rise to −40° C. during the addition. The resulting light orange solution was aged at −40° C. for 60 minutes and quenched by adding 1M citric acid (45 ml) and ethyl acetate (75 mL). The reaction was warmed to ambient temperature and the layers were separated. The organic layers were washed with 1M citric acid (45 mL). The reaction mixture was assayed by HPLC for percent conversion and product ee.

HPLC conditions: C-8 column, CH₃CN:water:phosphoric acid, isocratic elution 65:35:0.1 for 20 minutes, flow=1.0 ml/min, UV detection at 252 nm, st. material $t_R$=12.8 min, product $t_R$=10.3 min.

Chiral HPLC conditions: amylose stationary phase column, hexane:isopropanol 85:15 isocratic elution, flow= 1.0 ml/min, UV detection at 252 nm, st. material $t_R$=4.9 min, major enantiomer $t_R$=5.5 min, minor enantiomer $t_R$=25.0 min.

The enantiomeric excess was 96.5% and the reaction conversion was 93%, (6A% starting material). The assay yield was 85%. The product was purified by mixing in 10:1 heptane:toluene (65 mL) at 23° C. for 18 h. The product was isolated by filtration and oven dried at 35° C. to afford 9.5 gm (80%) of product as a light yellow powder.

EXAMPLE 6

Preparation of the Benzoxazinone

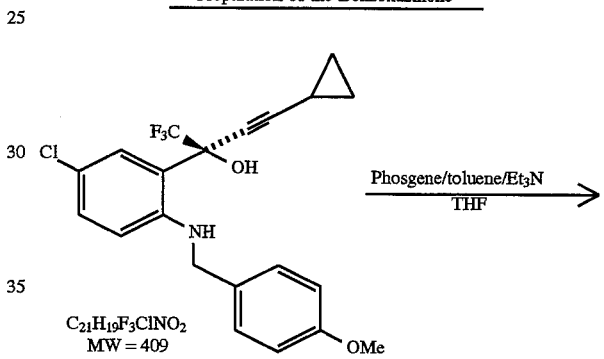

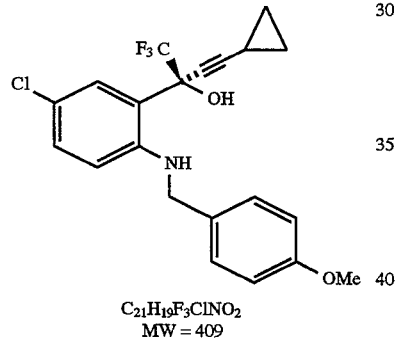

| Materials | Amt | mmol | MW |
|---|---|---|---|
| Ketone | 10 gm | 29.1 | 343 |
| 1R, 2S N-pyrrolidinyl norephedrine | 13.1 gm | 64 | 205 |
| cyclopropyl acetylene (d = 0.8) | 5.3 ml | 64 | 66 |
| n-BuLi (2.6M in cylohexane) | 50 mL | 125 | |
| THF (KF = 20 μg/ml) | 80 mL | | |
| 1M Citric acid | 90 mL | | |
| Ethyl acetate | 75 mL | | |

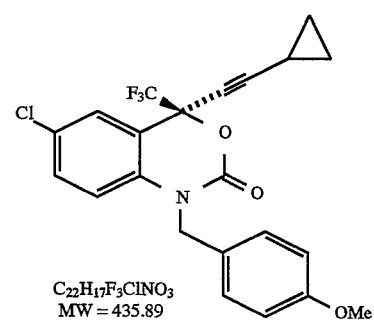

7

| Materials | Amt | mmol | MW |
|---|---|---|---|
| amino alcohol | 3.2 gm | 7.8 | 409 |
| Phosgene in toluene (1.93M) | 4.6 ml | 8.89 | |
| triethylamine (d = 0.726) | 5.4 ml | 39 | 101 |
| THF (KF ≦ 100 μg/ml) | 15 ml | | |
| D.I. water | 15 ml | | |
| EtOAc | 45 ml | | |
| hexanes | 30 ml | | |
| 1M citric acid | 40 ml | | |
| saturated brine | 25 ml | | |

The amino-alcohol was dissolved in THF (15 ml) and cooled to −10° C. under N₂. To the mixture was added triethylamine (5.4 ml) and phosgene in toluene (4.6 ml). The addition of phosgene caused an exotherm which was maintained below 20° C. by the rate of addition. The progress of the reaction was monitored by HPLC and was typically complete in 15 minutes.

HPLC conditions: C-8 column, $CH_3CN$:water:phosphoric acid, gradient elution from 50:50:0.1 to 90:10:0.1 over 20 minutes, flow=1.5 ml/min, UV detection at 252 nm, st. material $t_R$=14.6 min, product $t_R$=16.0 min.

The reaction was cooled to 0° C. and quenched with ice-cold water (15 ml) and ethyl acetate (20 ml). Saturated brine was used to break-up any emulsions. The organic layer was removed and the aqueous was extracted with ethyl acetate (15 ml). The combined organics were washed with 1M citric acid (40 ml) and saturated brine (25 ml). The organic was dried ($Na_2SO_4$) and concentrated in vacuo to afford 3.8 gm of a brown oil.

The product was crystallized from 5:1 hexane:ethyl acetate (25 ml), chilled to 0° C., aged for 1 h and filtered. The cake was washed with cold 5:1 hexane:ethyl acetate (2×5 ml). The cake was air dried with suction to afford 2.9 gm (85%) of a light orange solid.

EXAMPLE 7

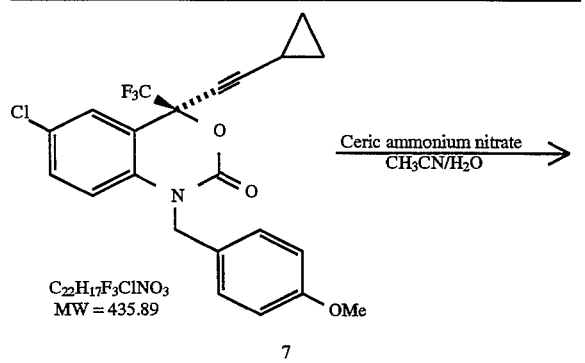

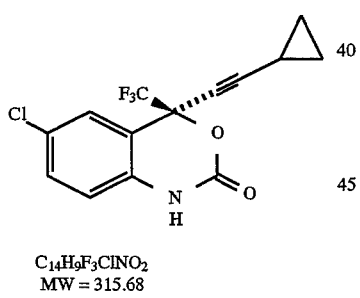

Compound A

| Materials | Amt | mmol | MW |
|---|---|---|---|
| PMB Compound A, 7 | 0.8 gm | 1.83 | 435 |
| Ceric ammonium nitrate | 4.4 gm | 8.0 | 548.23 |
| $CH_3CN$ | 15 ml | | |
| ethyl acetate | 30 ml | | |
| D.I. water | 30 ml | | |
| saturated brine | 10 ml | | |

The p-methoxybenzyl protected Compound A was dissolved in $CH_3CN$ (15 ml). To this solution was added a solution of ceric ammonium nitrate (4.4 gm) in water (5 ml). The reaction was typically complete in 2 h at 23° C. as determined by HPLC.

HPLC conditions: C-8 column, $CH_3CN$:water:phosphoric acid, gradient elution from 50:50:0.1 to 90:10:0.1 over 20 minutes, flow=1.5 ml/min, UV detection at 252 nm, st. material $t_R$=16.0 min, product $t_R$=9.0 min.

The reaction was diluted with D.I. water (5 ml) and concentrated to ca. ½ volume. The product was extracted from the resulting aqueous layer with ethyl acetate (2×15 ml). The combined organic was washed with D.I. water (2×10 ml) and brine (10 ml). The organic was concentrated in vacuo to afford a yellow gum. The product was isolated by silica gel chromatography.

REVERSE TRANSCRIPTASE ASSAY

The assay measures the incorporation of tritiated deoxyguanosine monophosphate by recombinant HIV reverse transcriptase (HIV $RT_R$) (or other RT) into acid-precipitable cDNA at the Km values of dGTP and poly r(C)•oligo $d(G)_{12-18}$. The inhibitors of the present invention inhibit this incorporation.

The assays were carried out in 55 mM Tris (pH 8.2)-30 mM KCl-30 mM $MgCl_2$-1 mM dithiothreitol-20 µg of $rC:dG_{12-18}$ (Pharmacia) per ml-8 mM [$^3$H]dGTP (New England Nuclear)-0.01% Triton X-100-50 mM ethylene glycol-bis(β-amino-ethyl ether)-N,N,N',N'-tetraacetic acid (EGTA)-1 mg of bovine serum albumin per ml. After 60 min of incubation at 37° C., acid-precipitable material was collected onto glass fiber filters by using a semiautomatic cell harvester. Bacterial cell extracts containing RT were diluted to within the linear range of the assay, and activity was determined in the presence and absence of inhibitor. Purified HIV-1 RT heterodimer produced in *E. coli* also served as a control. Results are determined as inhibitor concentration to give 50% inhibition ($IC_{50}$ wt), in nanomoles/liter. Compound A gave an $IC_{50}$ wt of 2 nM.

For the double mutant assay (dm), A17 RT was employed in the assay. A17 RT is resistant to various aminopyridones, as described in Nunberg, J. H. et al., *J. Virol.*, 65, 4887 (1991). Results are measured as $IC_{50}$ dm in nanomoles/liter. Compound A gave an $IC_{50}$ dm of 85 nM.

CELL SPREAD ASSAY

Inhibition of the spread of HIV in cell culture was measured according to Nunberg, J. H. et al., *J. Virol.*, 65, 4887 (1991). In this assay, MT-4 T-lymphoid cells were infected with HIV-1 (wild-type, unless otherwise indicated) by using a predetermined inoculum, and cultures were incubated for 24 h. At this time, ≦1% of the cells were positive by indirect immunofluorescence. Cells were then extensively washed and distributed into 96-well culture dishes. Serial twofold dilutions of inhibitor were added to the wells, and cultures were continued for 3 additional days. At 4 days postinfection, 100% of the cells in control cultures were infected. HIV-1 p24 accumulation was directly correlated with virus spread. The cell culture inhibitory concentration was defined as the inhibitor concentration in nanomoles/liter which reduced the spread of infection by at least 95%, or $CIC_{95}$.

While the foregoing specification teaches the principles of the present invention, with examples provided for the purpose of illustration, it will be understood that the practice of the invention encompasses all of the usual variations, adaptions, or modifications, as come within the scope of the following claims and its equivalents.

What is claimed is:

1. A process for the asymmetric synthesis of the chiral compound of the structure

19

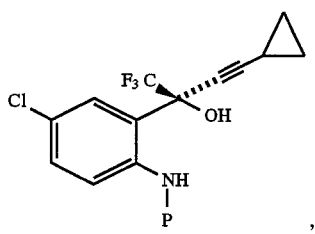

wherein P is an amino protecting group;
comprising the steps of:

(a) providing a mixture of excess (1R,2S)-N-substituted norephedrine, of the structure

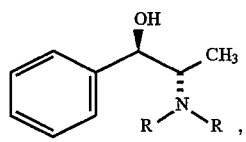

wherein R is $C_{1-4}$ alkyl, or —$NR_2$ forms pyrrolidinyl or piperidinyl;
with an excess of cyclopropylacetylene and an excess of a lithiating agent selected from n-butyllithium or sec-butyllithium or tert-butyllithium, at a temperature of between about –78° C. and about 10° C., in aprotic solvent;

(b) mixing with the mixture of Step (a) about one equivalent of reactant of the structure

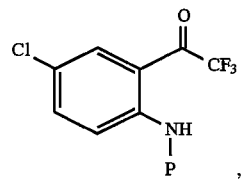

wherein P is an amino protecting group; and maintaining the resulting reaction mixture at a temperature between about –78° C. and about –20° C.;

(c) quenching by adding a proton source;

(d) to give the desired compound.

2. A process for the asymmetric synthesis of the chiral compound N-(4-methoxybenzyl)-6-chloro-2-[(R)-cyclopropylethynyl-hydroxy-trifluoromethyl]-methyl-aniline, of the structure

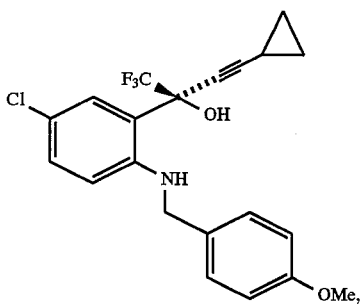

comprising the steps of:

(a) providing a mixture of excess (1R,2S)-N-substituted norephedrine, of the structure

20

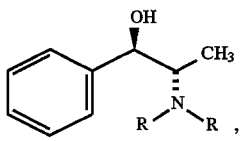

wherein R is $C_{1-4}$ alkyl, or —$NR_2$ forms pyrrolidinyl or piperidinyl;
with an excess of cyclopropylacetylene and an excess of a lithiating agent selected from n-butyllithium, sec-butyllithium or tert-butyllithium, at a temperature of between about –78° C. and about 10° C., in aprotic solvent;

(b) mixing with the mixture of Step (a) about one equivalent of reactant N-(4-methoxybenzyl)-6-chloro-2-(2-trifluoro-1-oxo-ethyl)-aniline, of the structure

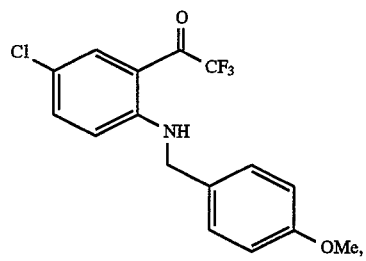

and maintaining the resulting reaction mixture at a temperature between about –78° C. and about –20° C.;

(c) quenching by adding a proton source;

(d) to give the desired compound.

3. A process for the asymmetric synthesis of the chiral compound of the structure

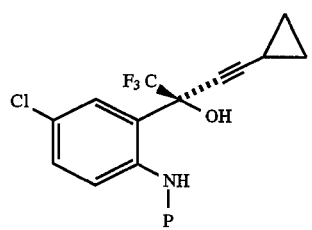

wherein P is an amino protecting group;
comprising the steps of:

(a) providing a mixture of excess (1R,2S)-N-pyrrolidinyl norephedrine, of the structure

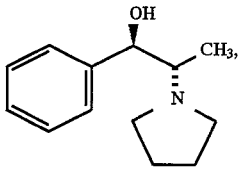

with an excess of cyclopropylacetylene and an excess of a lithiating agent selected from n-butyllithium or sec-butyllithium or tert-butyllithium, at a temperature of about –15° C., in aprotic solvent;

(b) mixing with the mixture of Step (a) about one equivalent of reactant of the structure

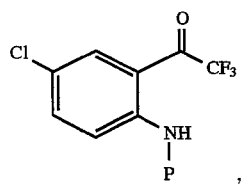

wherein P is an amino protecting group;
and maintaining the resulting reaction mixture at about −40° C.;

(c) quenching by adding a proton source;

(d) to give the desired compound.

4. A process for the asymmetric synthesis of the chiral compound N-(4-methoxybenzyl)-6-chloro-2-[(R)-cyclopropylethynyl-hydroxy-trifluoromethyl]-methyl-aniline, of the structure

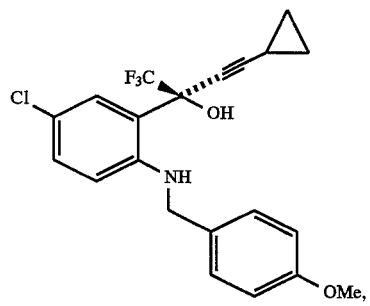

comprising the steps of:

(a) providing a mixture of excess (1R,2S)-N-pyrrolidinyl norephedrine, of the structure

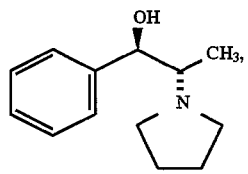

with an excess of cyclopropylacetylene and an excess of n-butyllithium, at a temperature of about −15° C., in aprotic solvent;

(b) mixing with the mixture of Step (a) about one equivalent of reactant N-(4-methoxybenzyl)-6-chloro-2-(2-trifluoro-1-oxo-ethyl)-aniline, of the structure

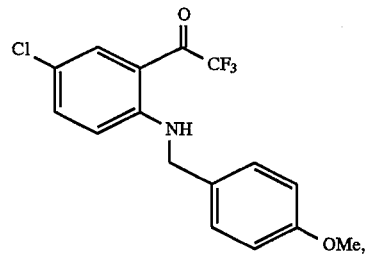

and maintaining the resulting reaction mixture at about −40° C.;

(c) quenching by adding a proton source;

(d) to give the desired compound, in ≧85% yield, ≧95% ee.

5. A process as in any of claims 1–2, wherein an additional heating step occurs between step (a) and step (b), that is, the mixture of step (a) is heated to between about −10° C. and about 10° C., for at least 5 minutes, then cooled to a temperature between about −78° C. and about −20 ° C., before step (b).

6. A process as in any of claims 3–4, wherein an additional heating step occurs between step (a) and step (b), that is, the mixture of step (a) is heated to between about −10° C. and about 0° C., for between about 10 minutes and about 60 minutes, then cooled to a temperature of at least about −40° C., before step (b).

* * * * *

UNITED STATES PATENT AND TRADEMARK OFFICE
CERTIFICATE OF CORRECTION

PATENT NO. : 5,633,405

DATED : 5/27/97

INVENTOR(S) : Andrew S. Thompson, Edward G. Corley, Edward J.J. Grabowski and Nobuyoshi Yasuda It is certified that error appears in the above-identified patent and that said Letters Patent is hereby corrected as shown below:

The Title of the Invention in Box 54 on the cover sheet, should read:

--ASYMMETRIC SYNTHESIS OF (-) 6-CHLORO-4-CYCLOPROPYL-ETHYNYL-4-TRIFLUOROMETHYL-1,4-DIHYDRO-2H-3,1-BENZOXAZIN-2-ONE

In Columm 1, lines 1-4, the Title of the Invention should read:

--ASYMMETRIC SYNTHESIS OF (-) 6-CHLORO-4-CYCLOPROPYL-ETHYNYL-4-TRIFLUOROMETHYL-1,4-DIHYDRO-2H-3,1-BENZOXAZIN-2-ONE

Signed and Sealed this

Twenty-seventh Day of January, 1998

*Attest:*

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO.    : 5,633,405
DATED         : May 27, 1997
INVENTOR(S)   : Andrew S. Thompson, Edward G. Corley, Edward J. J. Grabowski, Nobuyoshi Yasuda It is certified that error appears in the above-identified patent and that said Letters Patent is hereby corrected as shown below:

Column 3,
Lines 5 and 44, before "-chloro", delete "6" and insert therefor -- 4 --.

Column 4,
Line 49, before "chloro", insert -- 4- --.

Column 5,
Line 15 and 66, before "chloro", delete "6" and insert therefor -- 4 --.

Column 19, claim 2,
Line 48, before "-chloro", delete "6" and insert therefor -- 4 --.

Column 20, claim 2,
Line 17, before "-chloro", delete "6" and insert therefor -- 4 --.

Column 21, claim 4,
Line 16, before "-chloro", delete "6" and insert therefor -- 4 --.

Column 22, claim 4,
Line 7, before "-chloro", delete "6" and insert therefor -- 4 --.

Signed and Sealed this

Twenty-sixth Day of February, 2002

Attest:

Attesting Officer

JAMES E. ROGAN
Director of the United States Patent and Trademark Office